United States Patent
Nakao

(10) Patent No.: US 7,785,250 B2
(45) Date of Patent: *Aug. 31, 2010

(54) ENDOSCOPIC INSTRUMENT ASSEMBLY WITH SEPARABLE OPERATIVE TIP AND ASSOCIATED MEDICAL METHOD

(75) Inventor: Naomi L. Nakao, New York, NY (US)

(73) Assignee: Granit Medical Innovation, LLC, New York, NY (US)

( * ) Notice: Subject to any disclaimer, the term of this patent is extended or adjusted under 35 U.S.C. 154(b) by 1137 days.

This patent is subject to a terminal disclaimer.

(21) Appl. No.: 11/202,853

(22) Filed: Aug. 12, 2005

(65) Prior Publication Data

US 2007/0038022 A1 Feb. 15, 2007

Related U.S. Application Data

(63) Continuation of application No. 11/201,579, filed on Aug. 11, 2005.

(51) Int. Cl.
*A61B 1/00* (2006.01)
*A61B 18/14* (2006.01)
*A61B 17/06* (2006.01)

(52) U.S. Cl. .................. 600/104; 606/45; 606/222
(58) Field of Classification Search ................. 600/104, 600/45, 113, 222
See application file for complete search history.

(56) References Cited

U.S. PATENT DOCUMENTS

| | | | |
|---|---|---|---|
| 1,930,214 A * | 10/1933 | Wappler | 606/46 |
| 4,198,960 A * | 4/1980 | Utsugi | 600/104 |
| 5,290,284 A * | 3/1994 | Adair | 606/37 |
| 5,437,665 A | 8/1995 | Munro | |
| 5,782,748 A * | 7/1998 | Palmer et al. | 600/104 |
| 5,906,620 A * | 5/1999 | Nakao et al. | 606/113 |
| 6,004,273 A * | 12/1999 | Sakamoto et al. | 600/459 |
| 6,267,759 B1 | 7/2001 | Quick | |
| 6,358,259 B1 * | 3/2002 | Swain et al. | 606/148 |
| 7,402,162 B2 * | 7/2008 | Ouchi | 606/45 |
| 2004/0243108 A1 * | 12/2004 | Suzuki | 606/1 |

FOREIGN PATENT DOCUMENTS

WO    WO 98/01080    1/1998

* cited by examiner

*Primary Examiner*—Lee S Cohen
(74) *Attorney, Agent, or Firm*—R. Neil Sudol; Henry D. Coleman; William J. Sapone

(57) ABSTRACT

In an insertion configuration, an endoscope assembly includes an insertion member with a distal end face and a working channel and further includes an instrument shaft extending through the working channel and an operative tip connected to the instrument shaft and extending in a plane oriented perpendicularly to the instrument shaft. The operative tip is positioned along the distal end face of the endoscope insertion member. The operative tip is separable from the distal end face of the endoscope insertion member by a distally directed motion of the instrument shaft along the working channel.

8 Claims, 10 Drawing Sheets

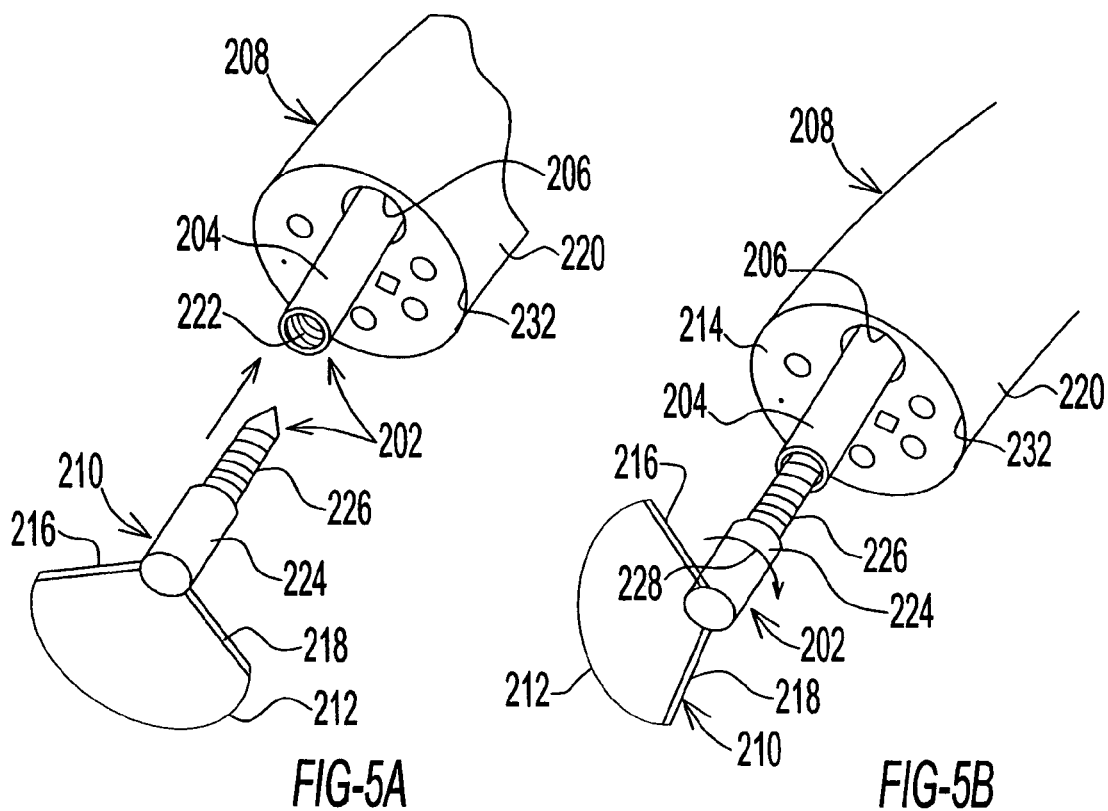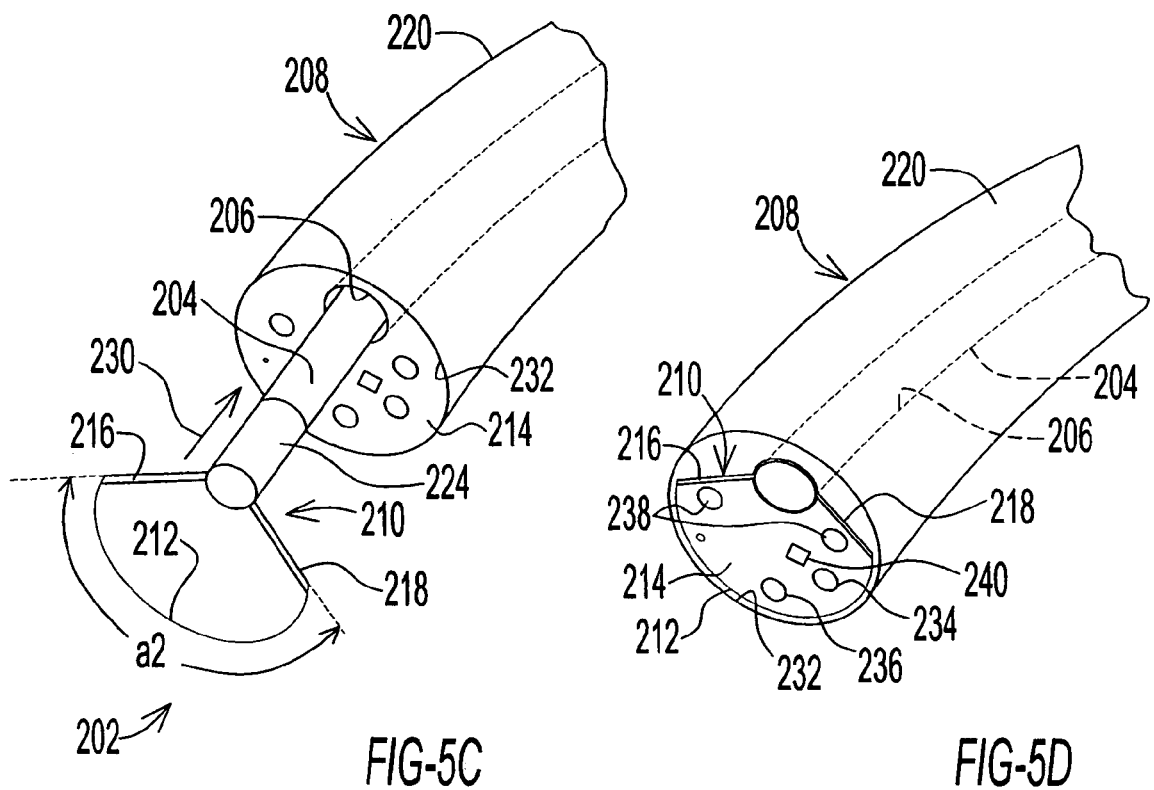

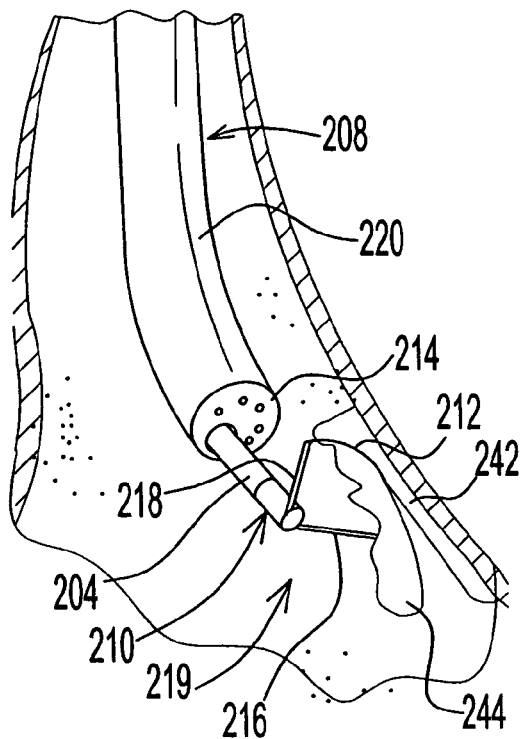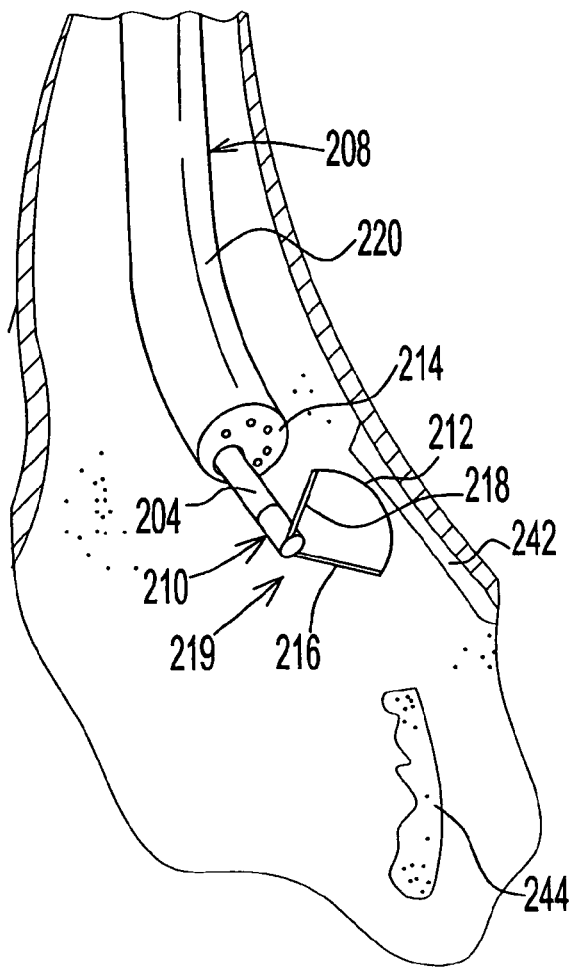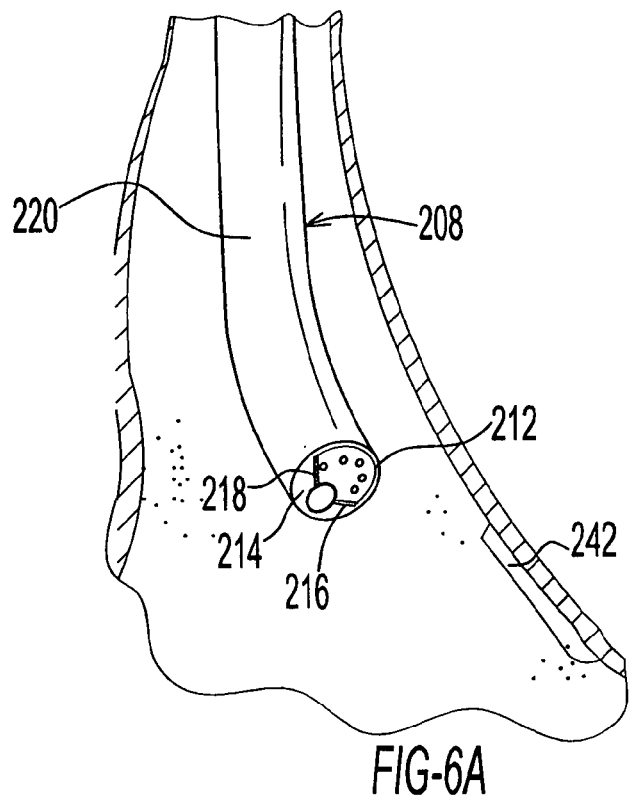

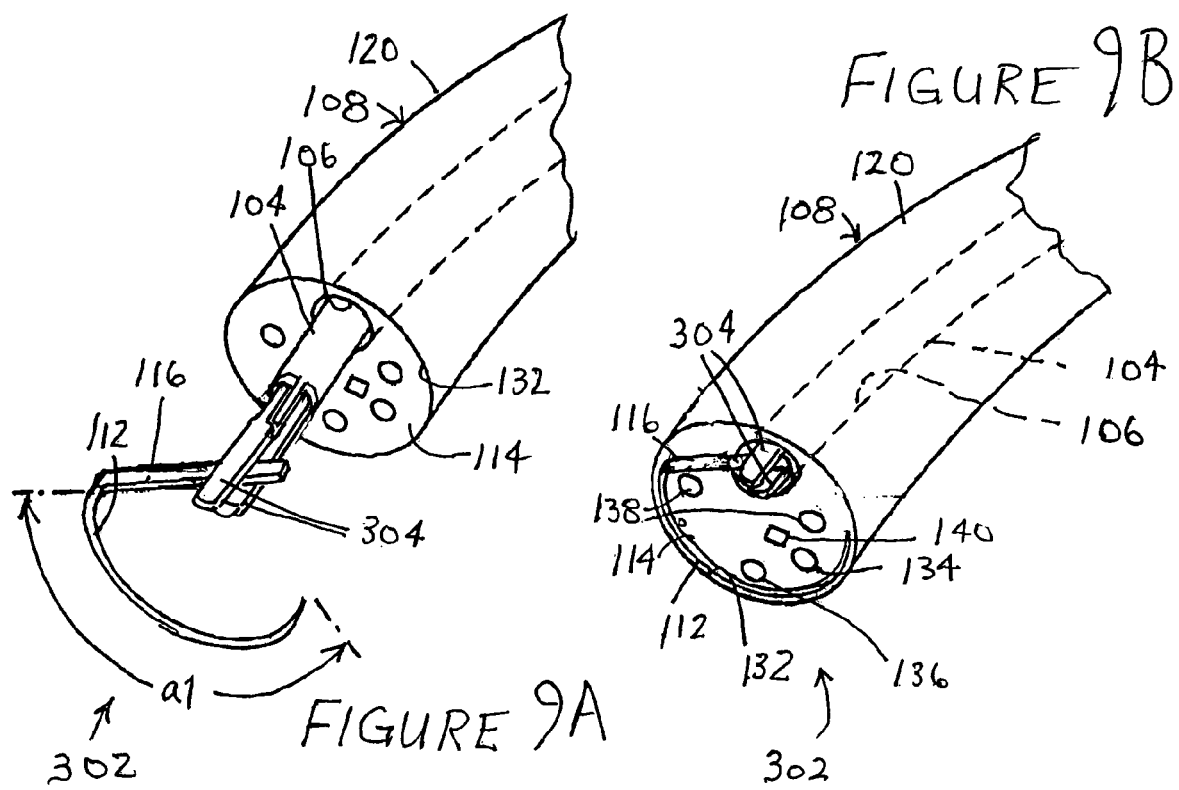

ENDOSCOPIC INSTRUMENT ASSEMBLY WITH SEPARABLE OPERATIVE TIP AND ASSOCIATED MEDICAL METHOD

CROSS-REFERENCE TO RELATED APPLICATION

This application is a continuation in part of application Ser. No. 11/201,579, filed Aug. 11, 2005.

BACKGROUND OF THE INVENTION

This invention relates to an endoscopic method. More particularly, this invention relates to a method utilizable with endoscopes to insert working instruments into a patient. This invention also relates to an associated instrument assembly. The invention is useful, for instance, in the treatment of Barrett's Esophagus and sessile colonic polyps.

The precancerous nature of high-grade dysplasia and the difficulty in detection of invasive carcinoma by endoscopy make esophagectomy and ablative therapy important considerations to treating those patients with this serious condition. The gold standard treatment for early esophageal cancer and high grade dysplasia is esophagectomy, the surgical removal of the diseased segment of the esophagus. This is an effective but drastic treatment and presents significant complications and lifestyle problems for the patient. Many patients are poor surgical candidates for this difficult surgery.

Endoscopic mucosal resection (EMR), the removal of mucosal tissue by use of a snare, is a therapeutic alternative and has become a standard treatment for patients with Barrett's Esophagus. This technique preserves the patient's esophagus while resecting the mucosa that is affected by this disease. A second method is tissue ablation with heat therapy. EMR is superior to tissue destruction because it permits pathologic evaluation of the resected specimen. Current endoscopic mucosal resection techniques for the treatment of esophageal cancer include strip biopsy, double snare polypectomy, with the combined use of saline and epinephrine injection. EMR may be curative if the primary tumor or dysplastic tissue is removed completely.

Another area where EMR may be used is for removal of large sessile polyps in the GI tract, primarily the colon. The malignant transformation potential of colorectal adenomatous polyps is well documented. Colonoscopic polypectomy is widely practiced in order to prevent the development of colon cancer. Sessile polyps are premalignant lesions that lay flatly on the mucosal surface of the colon wall. These lesions, in contrast to pedunculated polyps, are devoid of a stalk, and are broad based. The colon wall is composed of several layers: the mucosa (the surface layer), the submucosa, the muscularis (muscle layer), and the serosa (connective tissue layer). The thickness of the entire wall is 5 mm. When a cautery snare is used to remove a larger sessile lesion, it may catch part of the muscularis layer Cutting through the muscle layer causes a colonic perforation.

Devices currently used for EMR procedures are polypectomy snares and a variety of devices to assist in the use of these snares. For resection of dysplastic tissue in the esophagus the technique involves using two snares, one to hold up the targeted tissue and the other to sever that tissue. The use of saline solutions for injection beneath the target tissue is a common practice for the purpose of raising the tissue and creating a buffer layer. This process is called saline assisted polypectomy (SAP).

In the case of sessile colonic polyps, SAP is standard medical practice. The raised polyp is then severed with a polypectomy snare, often in several segments (segmental resection) depending on the size and location of the polyp.

The depth of the cut that occurs using the snare cautery device to remove dysplastic mucosal tissue is critical. As discussed above, if the cut is too deep, injuring the muscularis layer, a perforation may occur. Conversely, a cut too shallow may not remove enough of the affected tissue and therefore may require additional procedures, or worse, result in the development of metastatic cancer. Similar complications may occur during the removal of sessile colonic polyps. The colonic wall is approximately the same thickness as the esophageal wall, namely 5 mm. A perforation as a result of cutting into the muscularis layer will cause a colonic perforation, while a lesion that is not completely removed, either due to insufficient depth or breath, will result in recurrence of the dysplastic tissue. Repeated resections after a certain interval are recommended if the margin of resection achieved during the procedure is too close to the tumor. More than 2 mm of cancer clearance is required. The complications resulting from EMR as performed with today's devices and methods include perforation, bleeding, and strictures that occur from scar formation resulting from EMR procedures.

Ablation techniques rely on chemicals which, when combined with heat or freezing, destroy dysplastic tissue. Adverse reactions include destruction of the healthy tissue surrounding the lesion, allergic reactions to the chemicals and sensitivity to sun-light. Furthermore, all ablative techniques destroy the tissue and prevent adequate pathologic examination of the specimen.

An important limitation of surgical procedures performed through a flexible endoscope is the narrow working channel. Most endoscopes have a working channel with a diameter ranging from 2.3 to 3.4 millimeters in diameter. Thus, the instruments that one may pass through this channel must have an outer diameter smaller than the diameter of the working channel. In addition, the endoscope may go through convolutions and bends in the gastrointestinal tract, necessitating that the instrument be flexible. More specifically, the stiff length capable of being passed through an endoscope is 1.5 centimeters.

In the present state of the art, if a working distal end is required, which has a larger diameter than the working channel; such an instrument is affixed to the outer wall of the endoscope shaft, and passed into the patient alongside the endoscope. This makes for a much larger instrument which, in certain cases must be passed through the mouth, into the esophagus and stomach of the patient. Because the entryway into the esophagus does not accommodate such a large instrument, complications from passing such larger instrument abound. These include tearing of the upper esophageal sphincter muscle, and esophageal lacerations and perforations. Patients that undergo such invasive procedures require general anesthesia, and lengthier post operative care. These interventional procedures may only be performed by a handful of specialists, and are not available to the gastroenterologists at large. It would therefore be advantageous if one could find a way to advance an instrument with a larger working distal end into the gastrointestinal tract, and still be able to operate with such a device through the working channel of an endoscope.

OBJECTS OF THE INVENTION

It is an object of the present invention to provide a method for facilitating the insertion of a larger variety of instruments into a patient for use in an endoscopic procedure.

A more specific object of the present invention is to provide an endoscopic instrument assembly that facilitates the use of a larger distal working end than can pass through the working channel of an endoscope.

It is yet another specific object of the present invention to provide such an instrument assembly, which can be manipulated through the working channel of an endoscope.

A further object of the present invention is to provide a method for resecting dysplastic tissue masses disposed along internal organ walls.

It is a more particular object of the present invention to provide an instrument that will enable accurate removal of tissue that lies flatly on the mucosal wall of the gastrointestinal tract.

It is another more particular object of the present invention to provide such a method and/or instrument that reduces the likelihood of organ perforation.

It is another object of the present invention to provide such a method that is minimally invasive.

It is even a more particular object of the present invention to provide an instrument and accompanying method that enables control of the depth and breadth of resection.

A further object of the present invention is to provide such a method that is carried out endoscopically.

These and other objects of the invention will be apparent from the drawings and descriptions herein. Although every object of the invention is believed to be achieved by at least one embodiment of the invention, there is not necessarily any single embodiment that achieves all of the objects of the invention.

SUMMARY OF THE INVENTION

An insertion configuration of an endoscopic instrument assembly comprises, in accordance with the present invention, an endoscope having an insertion member with a distal end face and a working channel, an instrument shaft extending through the working channel, and an operative tip connected to the instrument shaft and extending in a plane oriented perpendicularly to the instrument shaft. The operative tip is positioned along the distal end face of the endoscope insertion member. The operative tip is separable from the distal end face of the endoscope insertion member by a distally directed motion of the instrument shaft along the working channel.

The operative tip may include an arcuate element, such as a cutting and/or cauterizing wire or a needle, positioned along a periphery of the distal end face of the endoscope insertion member. The operative tip may further include at least one support arm extending from the instrument shaft to the arcuate element. Typically, the operatively tip includes two support arms each connected at one end to the instrument shaft and at an opposite end to a respective end of the arcuate element.

Where the arcuate element is a cauterizing cutter made of an electrically conductive material, the instrument shaft includes an electrical conductor operatively coupled to the arcuate element. The support arms may be coated with an electrically insulating material to ensure that cauterization occurs only in tissues in contact with the arcuate element and not in tissues in contact with the support arms.

Pursuant to another feature of the present invention, the operative tip is connected to the instrument shaft via a separable coupling, such as a screw coupling.

The operative tip may be connected to the instrument shaft via a pivotable coupling or articulation. Means such as a slidable sheath or a wire may be operatively linked to the instrument shaft for rotating the operative tip relative to the instrument shaft about the pivotable coupling or articulation.

An endoscopic medical method in accordance with the present invention utilizes an endoscope having an insertion member with a working channel and a distal end face and further utilizes an instrument including an elongate shaft and an operative tip. The method comprises (a) inserting the shaft into the working channel, (b) placing the operative tip into engagement with and flush against the distal end face of the endoscope insertion member, (c) inserting, into a patient, the insertion member with the shaft extending in the channel and the operative tip in engagement with the endoscope end face, (d) thereafter shifting the instrument shaft in a distal direction along the working channel to separate the operative tip from the distal end face of the endoscope insertion member, and (e) using the separated operative tip to perform a medical procedure on internal tissues of the patient.

Where the operative tip is connected to the instrument shaft via a separable coupling, the method may further comprise connecting the operative tip to the instrument shaft after the inserting of the instrument shaft into the working channel. The connecting of the operative tip to the instrument shaft may include screwing the operative tip to the instrument shaft.

Where the operative tip is connected to the instrument shaft via a pivotable coupling or articulation, the method further comprises pivoting the operative tip relative to the instrument shaft after the inserting of the endoscope insertion member into the patient. The pivoting of the operative tip may include shifting a tubular member relative to the instrument shaft and over the pivotable coupling or articulation.

Where the operative tip includes an arcuate cauterizing cutter made of an electrically conductive material, the using of the operating tip includes drawing the arcuate cauterizing cutter along internal tissues of the patient while conducting current through the arcuate cauterizing cutter to thereby ablate a sheet or web of the internal tissues and cauterize the tissues.

BRIEF DESCRIPTION OF THE DRAWINGS

FIGS. 5A through 5D are schematic perspective views of a distal end portion of the endoscope of FIG. 4, showing successive steps in forming an insertion configuration of the cutting or cauterizing instrument together with the endoscope.

FIGS. 6A through 6C are schematic perspective views of the distal end portion of the endoscope of FIGS. 4 and 5A-5D, showing successive steps in the use of the instrument assembly in an endoscopic resection procedure, in accordance with the present invention.

FIG. 9A is a schematic perspective view, similar to FIG. 2C, of a distal end portion of an endoscope insertion member and an endoscopic instrument assembly, in accordance with the present invention, showing the instrument assembly with an operative tip in a use position separated from a distal end face of the endoscope insertion member.

FIG. 9B is a schematic perspective view, similar to FIG. 2D, of the distal end portion of the endoscope insertion member and the endocopic instrument assembly of FIG. 9A, showing the operative tip of the instrument assembly in a retracted insertion configuration disposed flush against the distal end face of the endoscope insertion member.

DETAILED DESCRIPTION

Figure 1:
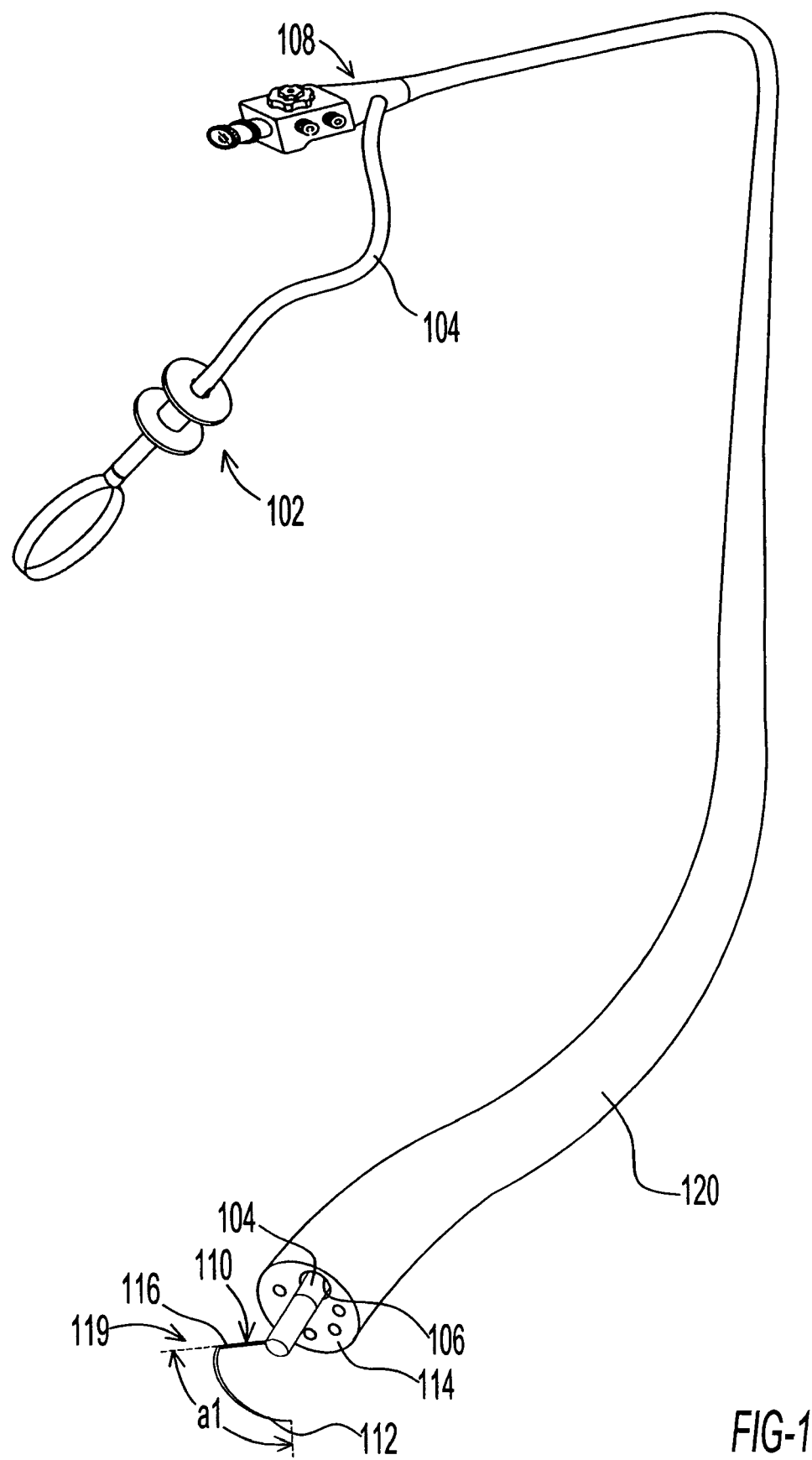
FIG. 1 is a schematic perspective view of an endoscope assembly including an embodiment of a surgical needle, pursuant to the present invention.

The following are definitions of some terms used in this disclosure.

The term "wire element" is used herein to denote a thin elongate cutting member that functions to ablate or otherwise cut organic tissues of a patient in a shaving procedure. Such a cutting element is preferably but not necessarily made of an electrically conductive material, generally a metal or alloy. In that case cutting and cauterizing is effectuated in large part by hear generated owing to the conduction of electrical current. Alternatively, the wire may cause cutting by freezing, or by slicing through tissue such as a cheese cutter would slice through cheese, simply by virtue of the wire's sharpness. A wire element as disclosed herein may be flexible or substantially rigid or semi-rigid. A semi-rigid wire element has some flexibility but has an inherent spring bias that tends to returns the wire to a preselected configuration, such as a circular arc. The wire element may be connected at spaced points to a holder member. The term "holder member" is used herein to denote a support for a wire element.

A principle underlying the medical methods and endoscopic surgical or diagnostic instrument assemblies disclosed herein is the detachability of a distal working end or operative tip of the instrument assemblies from the respective shafts and actuating handle assemblies. Thus, a flexible shaft may be passed as usual through a working channel of an endoscope prior to the initiation of an endoscopic procedure. At the distal end of the shaft is provided a male or female screw coupling, or another mechanism for adjoining another member. The shaft is inserted into the working channel of the endoscope scope from the proximal end thereof. Once the distal end of the shaft protrudes from the distal end of the working channel, the working end or operative tip is attached to the shaft.

It is also possible to insert an endoscopic instrument through an endoscope's working channel from the distal end "backwards" and to attach the proximal end of the instrument to a handle mechanism. It is already practiced in the industry to have a detachable handle. Pursuant to the present disclosure, the handle is detached, but the instrument is inserted in a proximal direction from the distal end of the endoscope insertion member, and the handle is then attached. To remove the endoscope from the patient, the distal end is again brought snuggly against the distal end face of the endoscope insertion member, and the endoscope is withdrawn.

Also, it may be necessary to rotate the distal tip of the endoscopic instrument relative to the endoscope insertion member to carry out the surgical or diagnostic procedure or to have the tip aligned properly with the distal end face of the endoscope so the instrument does not obstruct any of the vital members located at the tip. For this reason a rotating wire, such as a Nitinol wire or a combination Nitinol and stainless steel woven wire would be very useful, and could be incorporated in the device. Such material has a low friction surface such that when the wire is turned at a proximal end a distal end of the wire will turn in 1:1 correspondence to turns of the wire at the proximal end.

Once the instrument shaft is inserted through the working channel of the endoscope and the distal tip and handle properly coupled to the instrument shaft, the tip is oriented generally parallel to the distal end face of the endoscope. The instrument shaft is then pulled in the proximal direction through the endoscope working channel until the working assembly or operative tip fits flush with the distal end face of the endoscope. The distal end face of the endoscope contains one or two working channels, a cavity for pumping air into the patient, a lamp, a lens, and a nozzle for water. These features are distributed along the rather flat surface of the endoscope's distal end face. The working end or operative tip of the instrument assembly is designed to fit in among and around the operative features on the end face of the endoscope. There is a space around the perimeter of the endoscope end face that may accommodate, for instance, a thin arcuate cutting wire or a needle. Thus, when the instrument shaft is pulled in a proximal direction relative to the endoscope insertion member, placing the working assembly or operative tip of the instrument flush across the distal end face of the endoscope, there is no interference with the function or space of the endoscope operative features. As one would preferably not want the distal working end of the device to move out of position, a collet that contains the device guide wire could be rectangular or triangular so as to restrict the end member from rotating out of position and obstructing vital members of the endoscope's distal end-face. This could be incorporated in the instrument assembly of FIG. 7B by simply providing collet 268 with a rectangular lumen and making shaft 252 similarly rectangular.

When the endoscopist is handed the endoscope in order to insert it into the patient, all appears normal. The endoscopic surgical or diagnostic instrument is already placed in the working channel and does not interfere with visualization, water, air or suction. Only when the endoscopist is ready to resect tissue, does he or she push the instrument shaft in the distal direction along the endoscope working channel, thereby bringing the instrument into the picture for the first time.

As illustrated in FIGS. 1, 2A-2D, and 3A-3C, a medical sewing device 102 comprises an elongate instrument shaft 104 insertable through a working channel 106 of an endoscope 108, a holder member 110 provided at a distal end of the instrument shaft, and a needle element 112 connected to the holder member. Needle element 112 extends in cantilever fashion away from a free end of holder member 110 in a use configuration of the holder member and the wire element. Holder member 110 and needle element 112 are substantially rigid with respect to one another. Accordingly, the use configuration of holder member 110 and needle element 112 is identical to the insertion configuration, except for the location of the sewing device 102 relative to endoscope 108 and particularly relative to a leading or distal end face 114 thereof.

Holder member 110 typically takes the form of an arm 116, while needle element 112 is a circular section subtending an acute angle al from a tip or free end of holder or arm 116. Holder member 110 and needle element 112 comprise an operative tip 119 of instrument 102 and lie in a plane oriented perpendicularly to instrument shaft 104, at least during an insertion or deployment procedure. More particularly, holder member 110 and needle element 112 are disposed along and flush against distal end face 114 of endoscope 108 and inserted into a patient while riding on the distal end face of the endoscope insertion member 120.

Figures 2A, 2B:
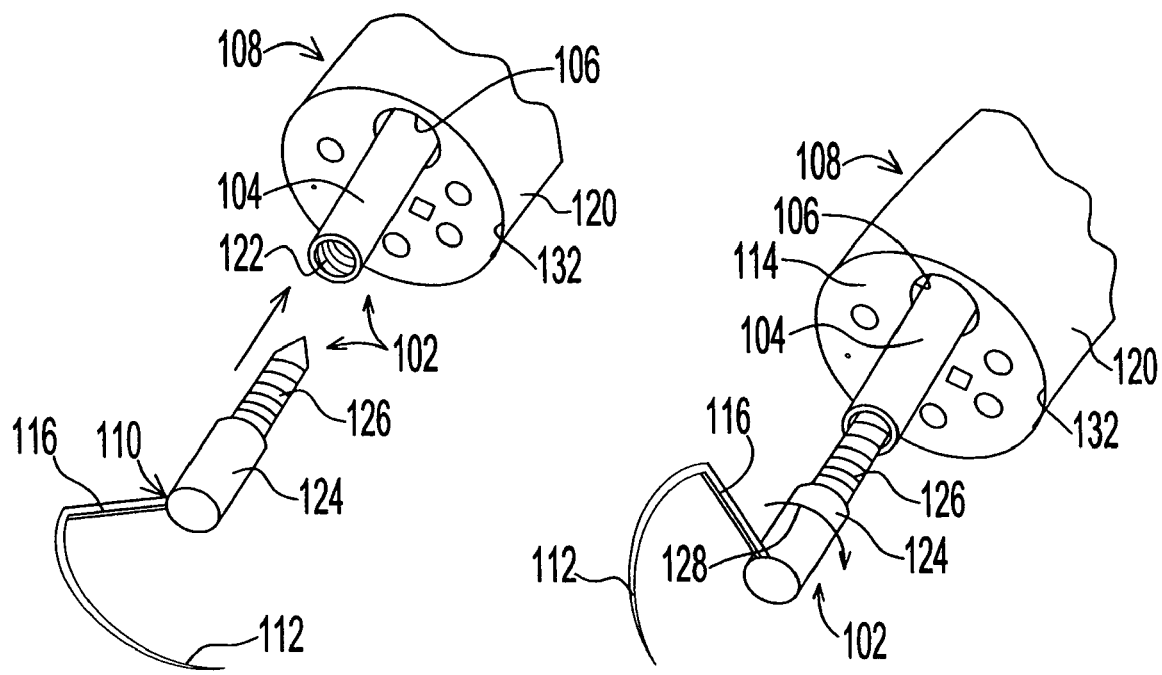
FIGS. 2A through 2D are schematic perspective views of a distal end portion of the endoscope of FIG. 1, showing successive steps in forming an insertion configuration of surgical needle together with the endoscope.
Figures 2C, 2D:
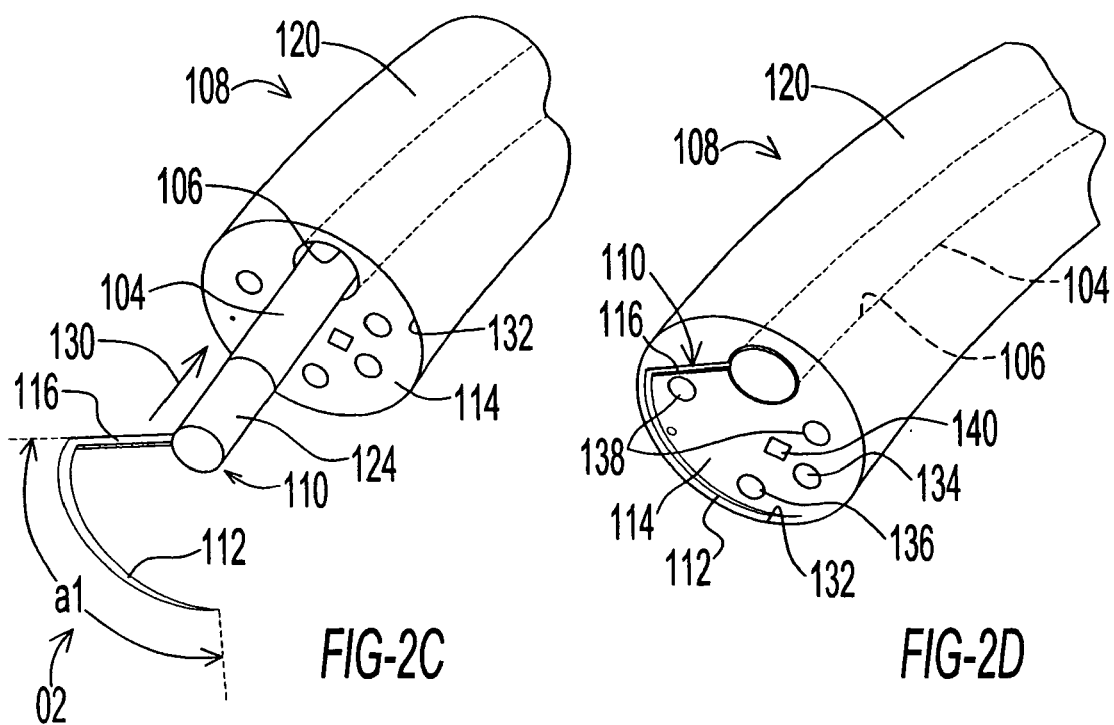

As shown in FIGS. 2A-2D, holder member 110 may be removably connectable to the end of instrument shaft 104. At the commencement of an endoscopic procedure, instrument shaft 104 is inserted into working channel 106 of endoscope 108 from the proximal end thereof. As shown in FIG. 2A, instrument shaft 104 is provided at a distal end with an internally threaded recess 122, while holder member 110 includes a stem 124 provided with an externally threaded pin 126. As indicated by an arrow 128 in FIG. 2B, holder member 110 is screwed to the distal end of instrument shaft 104 as it protrudes from the distal end of endoscope working channel 106. After formation of this connection, instrument shaft 104 is pulled in the proximal direction, as indicated by an arrow 130 in FIG. 2C, until holder member 110 and needle element 112 are snug against the leading or distal end face 114 of the endoscope insertion member 120, as shown in FIG. 2D. Holder member 110 and needle element 112 are dimensioned so that the needle is seated along a periphery or rim 132 of front or distal end face 114 and so that arm 116 misses or avoids various working elements on distal end face 114, including, for instance, an illumination outlet 134, a sensing lens 136, working channels 138, an irrigation fluid outlet port 140, etc. (FIG. 2D).

Figure 3B:
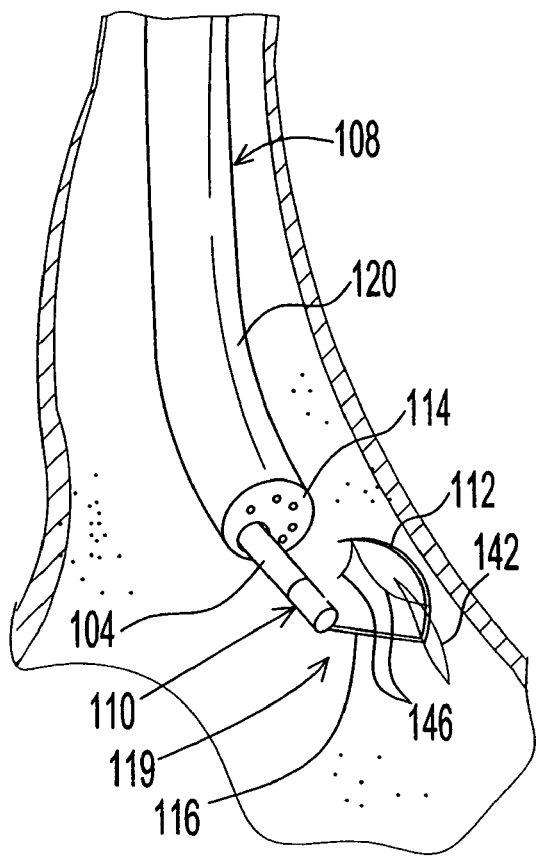
FIGS. 3A through 3C are schematic perspective views of the distal end portion of the endoscope of FIGS. 1 and 2A-2D, showing successive steps in the use of the instrument assembly in an endoscopic sewing procedure, in accordance with the present invention.
Figure 3C:
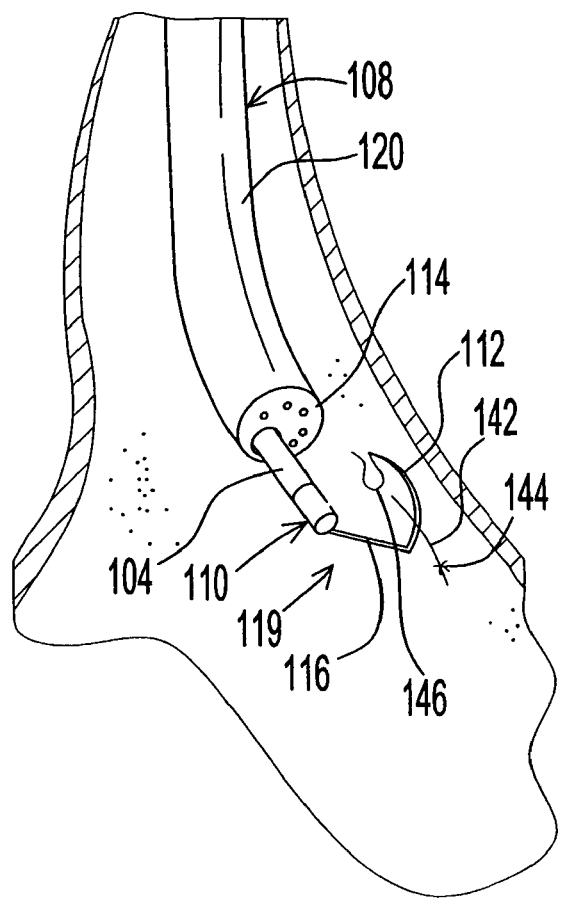
Figure 3A:
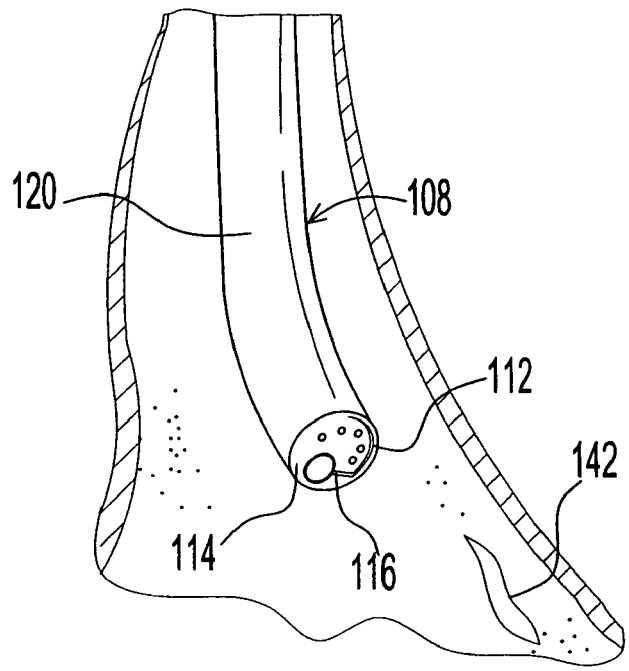
Figure 4:
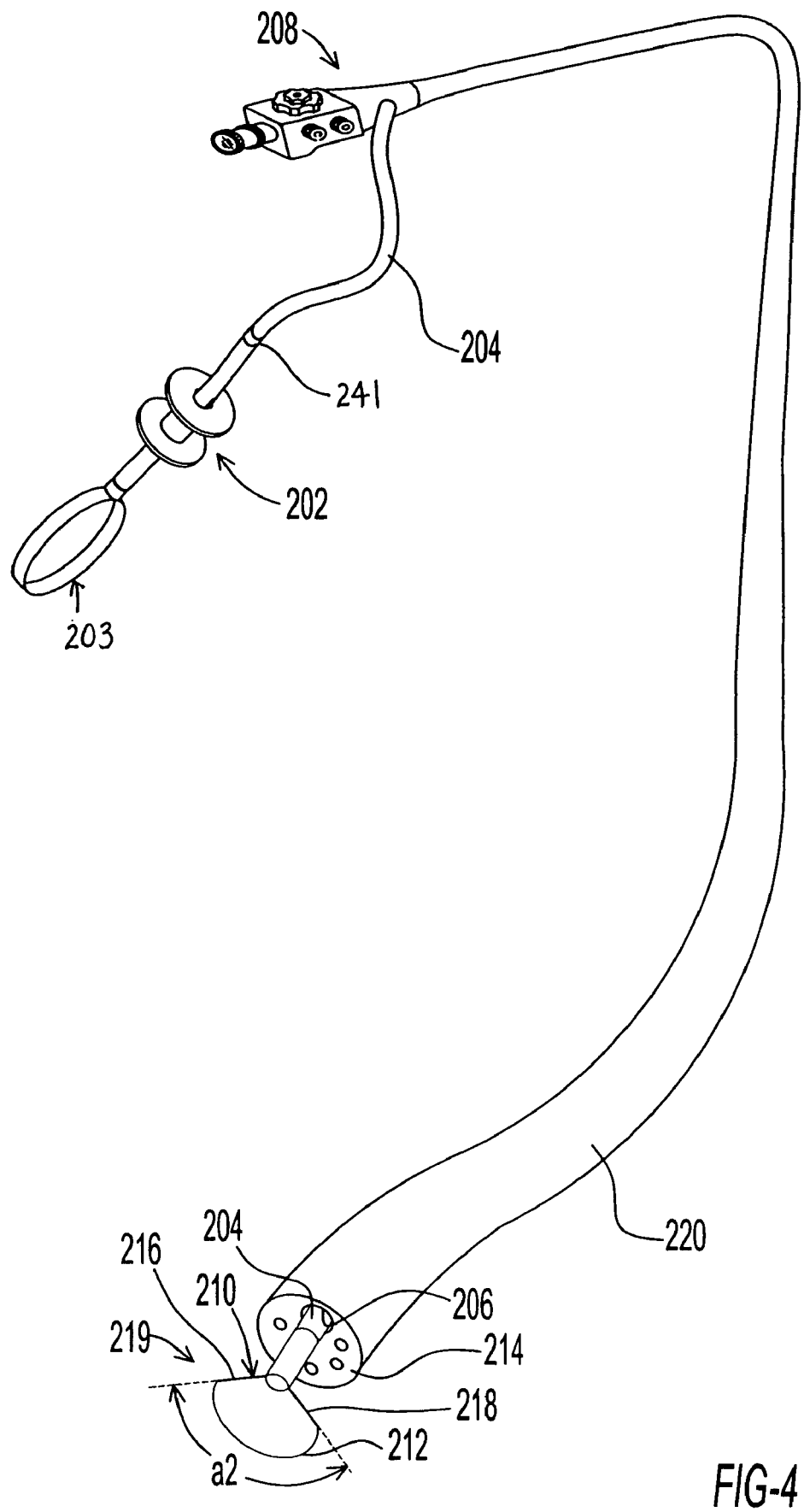
FIG. 4 is a schematic perspective view of an endoscope assembly including an embodiment of a cutting and cauterizing instrument, in accordance with the present invention.

Endoscope insertion member 120 is inserted into the patient with the operative tip 119 (holder member 110 and needle element 112) engaging the distal end face 114 of the endoscope 108, as shown in FIGS. 2D and 3A. After the endoscope has reached a diagnostic or surgical site inside the patient, for instance, a wound or incision 142 (FIG. 3A), shaft 104 is pushed in the distal direction along the endoscope working channel 106 so that operative tip 119 is separated from distal end face 114 of the endoscope insertion member 120, as shown in FIGS. 2C and 3B. Then, instrument 102 and endoscope 108 are manipulated form outside the patient to bring needle element 112 into engagement with tissues on one side of wound or incision 142. Needle element 112 is inserted through the tissues opposite sides of wound or incision 142, as shown in FIG. 3B. The inserting of needle element 112 into the tissues along wound or incision 142 may include rotating instrument shaft 104 from outside the patient. Needle 112 or a suture thread 146 entrained to the needle element could be introduced into the tissue, and then gripped by a grasper (not shown) that is deployed via another endoscope inserted next to the first one, or through another working channel in the same endoscope After the completion of a sewing stitch 144 as shown in FIG. 3C, the process may be repeated until the entire wound or incision 142 is stitched shut. An endoscopic graspers or other device (not shown) may be used to in conjunction with needle element 112, for instance via a second working channel 138 of the endoscope, to manipulate a suture thread 146 to form stitches 144.

As illustrated in FIGS. 4, 5A-5D, and 6A-6C, a medical cutting and cauterizing device 202 comprises a handle assembly 203, an elongate instrument shaft 204 insertable through a working channel 206 of an endoscope 208, a holder member 210 provided at a distal end of the instrument shaft, and a cutting and cauterization wire element 212 connected to the holder member. Wire element 212 may be made of tungsten. Wire element 212 may alternatively be made of a semi-rigid stainless steel, and cut through tissue without cauterization action. Wire element 212 extends between spaced points of holder 210 member in a use configuration of the holder member and the wire element. In this embodiment, the use configuration of holder member 210 and wire element 212 is identical to the insertion configuration, except for the location of the cutting and/or cauterizing device 202 relative to endoscope 208 and particularly relative to a leading or distal end face 214 thereof. This is to say that holder member 210 and wire element 212 are substantially rigid components connected to one another in a fixed configuration.

Holder member 210 typically but not necessarily has a V-shaped configuration with a pair of arms 216 and 218 extending at an angle a2 relative to one another. Wire element 212 extends along a circular arc from a tip or free end of arm 216 of the holder member to a tip or free end of arm 218. Holder member 210 and wire element 212 comprise an operative tip 219 of instrument 202 and lie in a plane oriented perpendicularly to instrument shaft 204, at least during an insertion or deployment procedure. More particularly, holder member 210 and wire element 212 are disposed along and flush against distal end face 214 of endoscope 208 and inserted into a patient while riding on the distal end face of the endoscope insertion member 220.

As shown in FIGS. 5A-5D, holder member 210 may be removably connectable to the end of instrument shaft 204. At the commencement of an endoscopic procedure, instrument shaft 204 is inserted into working channel 206 of endoscope 208 from the proximal end thereof. As shown in FIG. 5A, instrument shaft 204 is provided at a distal end with an internally threaded recess 222, while holder member 210 includes a stem 224 provided with an externally threaded pin 226. As indicated by an arrow 228 in FIG. 5B, holder member 210 is screwed to the distal end of instrument shaft 204 as it protrudes from the distal end of endoscope working channel 206. After formation of this connection, instrument shaft 204 is pulled in the proximal direction, as indicated by an arrow 230 in FIG. 5C, until holder member 210 and wire element 212 are snug against the leading or distal end face 214 of the endoscope insertion member 220, as shown in FIG. 5D. Holder member 210 and wire element 212 are dimensioned so that the wire element is seated along a periphery or rim 232 of front or distal end face 214 and so that arms 216 and 218 miss or avoid various working elements on distal end face 214, including, for instance, an illumination outlet 234, a sensing lens 236, another working channel 238, an irrigation fluid outlet port 240, etc. (FIG. 5D).

As an alternative to the separable coupling of holder member 210 to the distal end of instrument shaft 204, handle assembly 203 may be removably connected to the proximal end of shaft 204 via a separable coupling 241 (FIG. 33). In that case, shaft 204 is inserted through working channel 206 from the distal end thereof and subsequently handle assembly 203 is connected to the proximal end of the instrument shaft, after it emerges from the proximal end of working channel 206. In this embodiment, operative tip 219 may be rigidly and inseparably secured to the distal end of the instrument shaft 204.

Endoscope insertion member 220 is inserted into the patient with the operative tip 219 (holder member 210 and cauterizing wire element 212) engaging the distal end face 214 of the endoscope 208, as shown in FIGS. 5D and 6A. After the scope has reached a diagnostic or surgical site inside the patient, for instance, a tissue mass 242 (FIG. 6A) such as in Bartlett's esophagus, shaft 204 is pushed in the distal direction along the endoscope working channel 206 so that operative tip 219 is separated from distal end face 214 of the endoscope insertion member 220, as shown in FIGS. 5C and 6B. Then, instrument 202 and endoscope 208 are manipulated form outside the patient to bring wire element 214 into engagement with tissue mass 242. Wire element 212 is drawn into and along tissue mass 242 to remove a thin layer or web 244 of the tissue, as shown in FIG. 5B. During the motion of wire element 212 through tissue mass 242, electrical current is conducted into the wire element to facilitate a cutting and cauterizing of the tissue. The drawing of wire element 212 into and along the tissue mass 242 may then include pulling the holder member 210 via shaft 204 from outside the patient to draw the wire element towards a distal end face of the endoscope. Alternatively, the entire endoscope with shaft 204 and holder member 210 entrained thereto may be moved in the proximal direction. In certain cases, the motion may be that of a pushing away rather than pulling of either the endoscope, the cutting device or both. After the separation of tissue layer or web 244, as shown in FIG. 6C, the process may be repeated until the entire undesirable tissue mass 242 is removed from organ wall 245. A retrieval net or other device (not shown) may be used to remove the separated tissue slices or webs 244 from the patient.

Figure 7B:
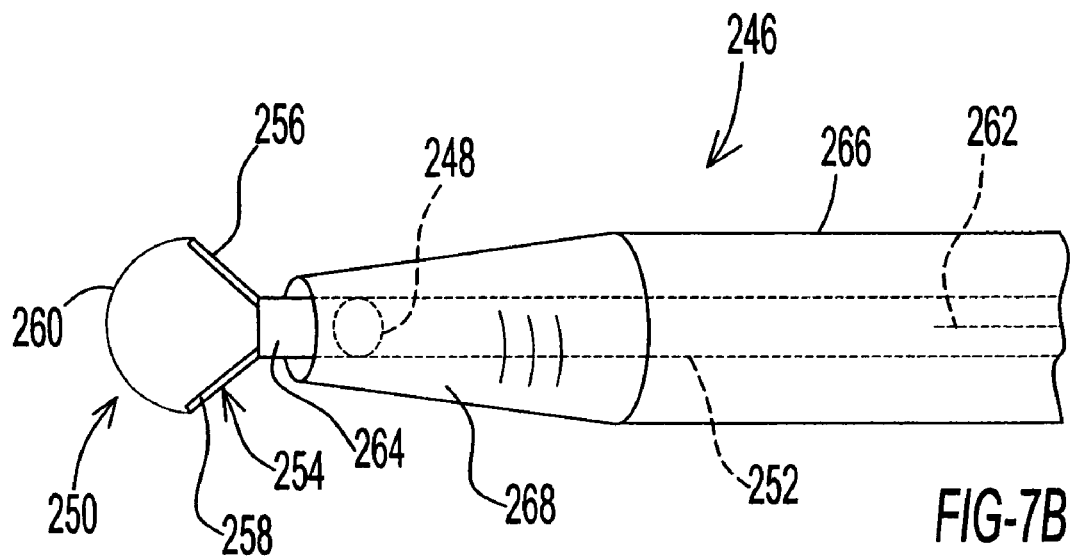
FIGS. 7A and 7B show successive steps in utilization of a modification of the cutting and cauterizing instrument assembly of FIGS. 4, 5A-5D, and 6A-6C.
Figure 7A:
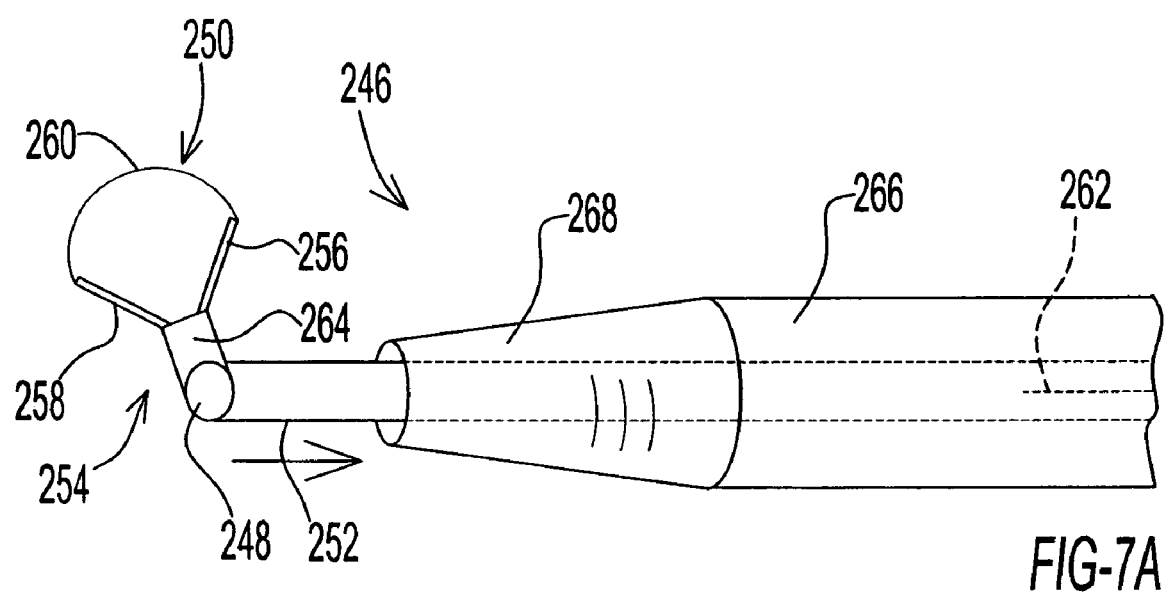

As depicted in FIGS. 7A and 7B, a cutting and cauterizing instrument or device 246 as described above with reference to FIGS. 4-6C may be provided with a joint or articulation 248 that enables a user to pivot an operative tip 250 from a transverse orientation (FIG. 7A) relative to an instrument shaft 252 to a parallel or longitudinal orientation (FIG. 7B) relative to the instrument shaft. In the transverse orientation, the operative tip 250, including a Y-shaped holder 254 with a pair of arms 256 and 258 and an arcuate wire element 260 extending between the arms, is disposable in contact with a front or distal end face of an endoscope (not shown). In the parallel orientation, the operative tip 250 extends in a plane (plane of drawing FIG. 7B) that is parallel to a longitudinal axis 262 of instrument shaft 252. Operative tip 250, including holder 254 and a stem piece 264, may be spring biased towards the transverse orientation. Pivoting of the operative tip 250 to the parallel orientation is effectuated, for instance, by sliding shaft 252 axially relative to a surrounding sheath 266. As joint or articulation 248 is moved into sheath 266, stem piece 264 assumes a collinear relationship with shaft 252. In another embodiment, one or more wires or rods (not shown) may extend along shaft 252 to a distal end of stem piece 264 for exerting a torque thereon. The wires or rods may be alternately pushed or pulled, to change the orientation of the operative tip 219 from transverse to parallel and back again.

A metal collet 268 may be provided at the distal end of sheath 266 to facilitate the transformation from the transverse orientation of FIG. 7A to the parallel orientation of FIG. 7B. When the endoscopist is ready to pull the endoscope 208 out of the patient, operative tip 219 may stay in the parallel position, just as a cauterization snare with a pouch and a polyp may be pulled out without creating a problem.

Figure 8B:
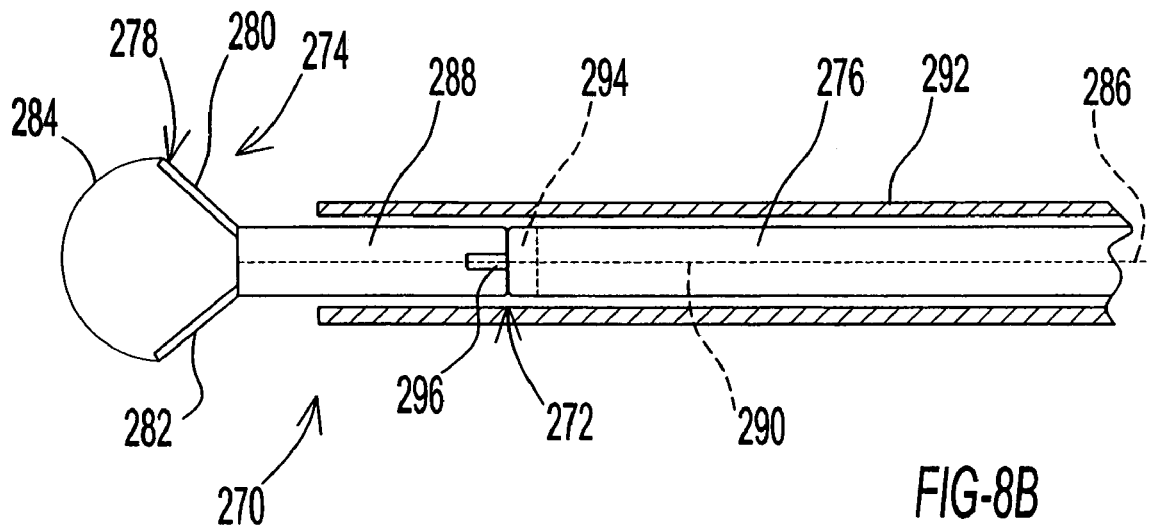
FIG. 8B is a schematic side elevational view of the cutting and cauterizing instrument assembly of FIG. 8A, showing a straightened configuration of the assembly.
Figure 8A:
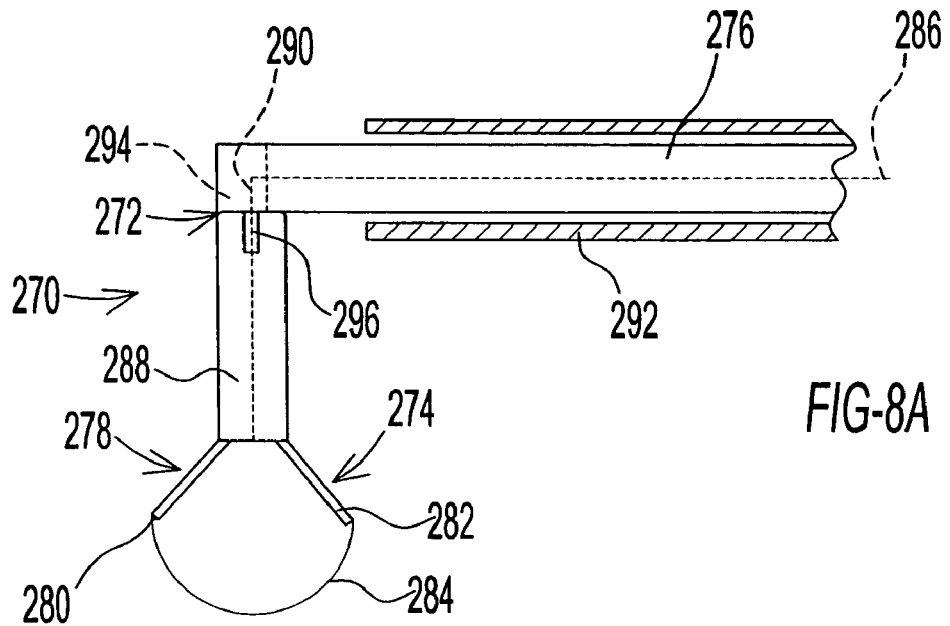
FIG. 8A is a schematic side elevational view, partially in cross-section, of a modification of the cutting and cauterizing instrument assembly of FIGS. 7A and 7B, showing a transverse or angled configuration of the assembly.
Figure 8C:
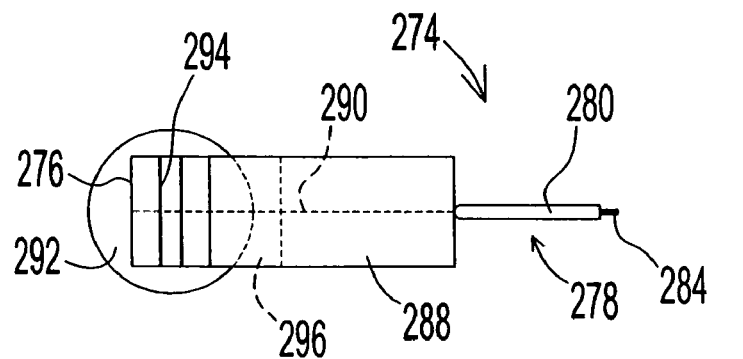
FIG. 8C is a schematic end elevational view of the cutting and cauterizing instrument assembly of FIG. 8A, taken from the left side in FIG. 8A.

As depicted in FIGS. 8A through 8C, a cutting and cauterizing instrument or device 270 as described above with reference to FIGS. 4-6C may be provided with a joint or articulation 272 that enables a user to pivot an operative tip 274 from a transverse orientation (FIG. 8A) relative to an instrument shaft 276 to a parallel or longitudinal orientation (FIG. 8B) relative to the instrument shaft. In the transverse orientation, the operative tip 274, including a Y-shaped holder 278 with a pair of arms 280 and 282 and an arcuate wire element 284 extending between the arms, is disposable in contact with a front or distal end face of an endoscope (not shown). In the parallel orientation, the operative tip 274 extends in a plane (plane of drawing FIG. 8B) that is parallel to a longitudinal axis 286 of instrument shaft 276. Operative tip 274, including holder 278 and a stem piece 288, are maintained in either the transverse orientation (FIG. 8A) or the parallel or straightened orientation by an elongate elastic member 290 that extends through a longitudinal bore or channel (not separately depicted) in instrument shaft 276 and through a longitudinal bore or channel (not shown) in stem piece 288. Pivoting of the operative tip 274 to the straightened orientation is effectuated, for instance, by sliding shaft 276 axially relative to a surrounding sheath 292. As joint or articulation 272 is moved into sheath 292, stem piece 288 assumes a collinear relationship with shaft 276.

A distal end (not separated labeled) of instrument shaft 276 is provided with a transverse slot 294, while a proximal end of stem piece 288 is optionally provided with a transverse slot 296. Slots 294 and 296 accommodate and facilitate a shifting of elastic member 290 during a rotation of stem piece 288 from the transverse orientation to the parallel or straightened orientation.

Wire element 212 may be constructed as a semicircle, or ¾ of a circle, and even as a straight cutting wire. The arcuate shape of wire element 212 is optimal for working in the esophagus, which has a rather restricted, circular lumen. The lesion may be removed by bringing the instrument below the lesion, and slowly burning off thin layers of tissue. The process may be quite controlled as to depth and breath. Clean margins are now created, no gaps need occur, and the muscularis need never be invaded and breached.

The EMR procedure sometimes requires injection of saline to raise the area for creating a buffer, or for injection of dye to mark the spot. It is therefore advantageous to provide either a double lumen that would house the shaft and instrument 202 in one lumen and a needle in another, or one lumen that would house them both. A snare with a web member may also be included in the assembly, preferably in a second or third lumen if the web member is to include a tether.

The cutting and cauterizing instrument 202 is quite advantageous for EMR of sessile colonic polyps. The procedure may be performed as described above. The endoscope 208 can be bent 360 degrees in a circular motion, allowing for good contact and control. However, it may become desirable at a certain point, especially in the case of colonic polyps located in and around a bend in the colon or other lesions that are difficult to reach, to have the operative tip 219 device convert from a perpendicular (transverse) to a vertical (parallel) position, as described hereinabove with reference to FIGS. 7A and 7B. Such an instrument may not be used while the endoscope 208 is being inserted, because having the operative tip 219 in a parallel or vertical position will block the endoscopist's view and interfere with insertion of the endoscope.

As it is important that the operative tip 119, 219 does not move out of place while the endoscope 108, 208 is being inserted into the patient, stems 124, 224 and posts or arms 116, 216, 218 are constructed such that there is a snug fit of the stems 124, 224 into the distal ends of the working channels 106, 206. In addition, by pulling the device 102, 202 until the operative tip 119, 219 is in snug engagement with the endoscope tip, there is no opportunity for the distal assembly to be displaced during the insertion procedure.

Instrument 202 is quite advantageous for EMR of sessile colonic polyps. The procedure may be performed as described above. The endoscope 208 can be bent 360 degrees in a circular motion, allowing for good contact and control. However, it may become desirable at a certain point, especially in the case of colonic polyps located in and around a bend in the colon or other lesions that are difficult to reach, to have the operative tip 219 device convert from a perpendicular (transverse) to a vertical (parallel) position, as described hereinabove with reference to FIGS. 7A and 7B. During insertion of an endoscope the operative tip cannot be disposed in a parallel or vertical position as such a position will block the endoscopist's view and interfere with insertion of the endoscope. Instead, the operative tip must lie flat in a perpendicular (to the working channel and the instrument shaft) orientation, along the end face of the endoscope.

As it is important that the operative tip does not move out of place while the endoscope is being inserted into the patient, the stems and posts or arms are constructed such that there is a snug fit into the working channel of the distal end of the instrument shaft, such as stem. This is accomplished by making this distal instrument shaft portion larger that the main body of the shaft. In addition, by pulling the device until the operative tip is in snug engagement with the endoscope tip, there is no opportunity for the distal assembly to be displaced during the insertion procedure. Additionally, the collet may be rectangular, triangular or shaped in a way as to not allow a similarly fitting instrument shaft to rotate and obstruct the vital members of the distal tip of the endoscope.

A device may be offered with one shaft with handle, and several working-end assemblies to be attached as per the requirement of the surgeon. The handle assembly includes a plug for cautery, which is activated when surgery is performed. This idea is novel in the art of interventional flexible endoscopy: there are no devices at present that may be operated through the working channel of a flexible endoscope, which possess a substantially rigid end-working assembly that is larger than the working channel. This invention enables the use of such a larger end-assembly by passing the shaft of the instrument into the endoscope's working channel, and then attaching the end assembly distally prior to insertion into the patient. The end assembly must be "invisible" to the endoscopist until he or she are ready to use it. At that point the device is pushed forward, comes into view, and may be utilized for the operation.

In using the medical sewing assembly 102 of FIGS. 1 through 3C, one must use an endoscopic grasper instrument via a second working channel of the endoscope (or a second endoscope) in order to manipulate the suture thread 146 to properly form stitches 144. FIGS. 9A and 9B depict a variation of the medical sewing device and instrument assembly of FIGS. 1 through 3C, which easier to manipulate. Reference numerals in FIGS. 9A and 9B are the same as reference numerals in FIGS. 1 through 3C where the designated elements are substantially identical.

FIGS. 9A and 9B depict an endoscopic instrument assembly 302 for sewing or stitching organic tissue of a patient wherein needle 112 and holder or arm 116 are separably couplable to instrument shaft 104 by virtue of a pair of grasper jaws 304 pivotably connected to the distal end of shaft 104. FIG. 9B illustrates an insertion configuration of instrument assembly 302 wherein grasper jaws 304 grip holder arm 116 and shaft 104 is retracted in a proximal direction through working channel 106 of endoscope insertion member 108, thereby bringing needle 112 into contact with distal end face 114 of the endoscope insertion member. During passage of the distal end portion of endoscope insertion member 108 along a lumen of an internal body organ in an insertion or deployment procedure, grasper jaws 304 are maintained in a closed configuration locking holder arm 116 thereto and instrument shaft is pulled in a proximal direction relative to endoscope insertion member 108. This maintains needle 112 disposed along periphery 132 of endoscope distal end face 114.

Figure 10:
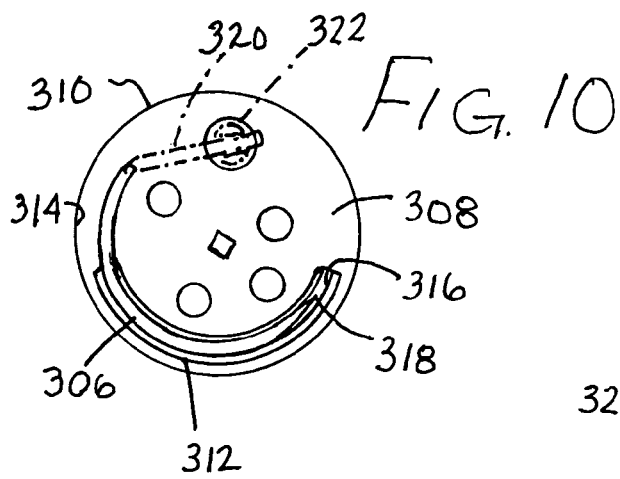
FIG. 10 is a schematic front end elevational view of an endoscope insertion member with an instrument assembly having an operative tip disposed on the front face of the endoscope insertion member.

FIG. 10 illustrates a modification of the instrument assembly of FIGS. 9A and 9B. A needle 306 is held to a distal end face 308 of an endoscope insertion member 310 via a magnetic holder 312. Needle 306 is made at least partly of a magnetic material such as stainless steel. Holder 312 is a circular section that is adhesively attached to distal end face 308 about a periphery 314 thereof. Holder 312 may be formed with an arcuate groove 316 that serves as a seat for at least a portion of needle 306. Needle 306 is preferably provided at a rear end, opposite a sharp needle point 318 with a holder or arm 320 that may be gripped by a grasper instrument 322.

Figure 11:
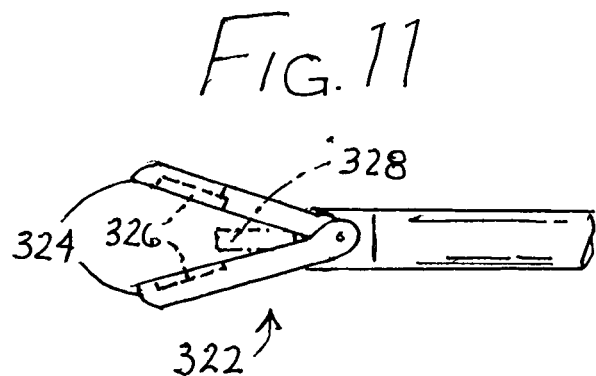
FIG. 11 is a partial schematic side elevational view of a grasper in accordance with a feature of the present invention.

As shown in FIG. 11, grasper 322 has a pair of jaws 324 one or both of which is provided with a magnet 326 for facilitating the recovery of needle 306 once it has been dropped in an internal organ or cavity of a patient. Alternatively, a magnetic element 328 may be disposed between jaws 324, extending from the joint or pivot point of the jaws. Where a magnetic capture is contemplated, the needle may be only partially made of a magnetic metal, on the ends of the needle. The magnetic material may be a coating applied to a nonmagnetic material such as nitinol.

Figure 12:
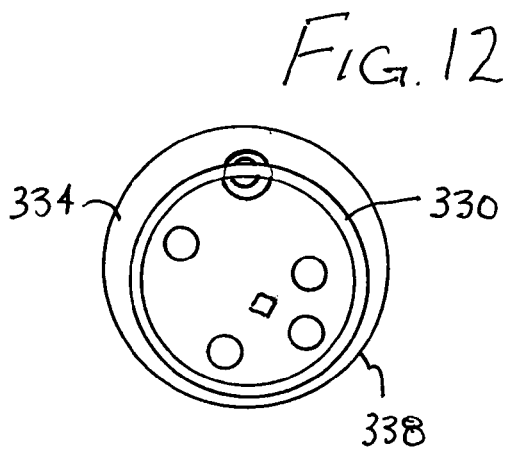
FIG. 12 is a schematic front end elevational view of an endoscope insertion member with another instrument assembly having an operative tip disposed on the front face of the endoscope insertion member.
Figure 13:
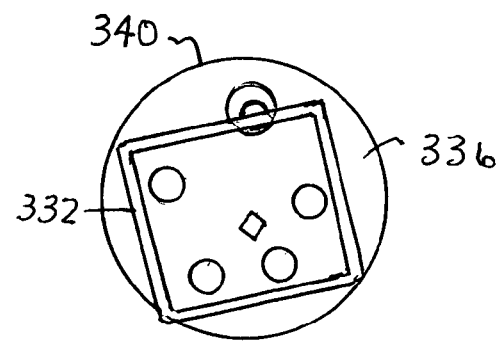
FIG. 13 is a schematic front end elevational view of an endoscope insertion member with yet another instrument assembly having an operative tip disposed on the front face of the endoscope insertion member.

FIGS. 12 and 13 respectively depict a circular shape 330 and a square or rectangular shape 332 of respective operative endoscopic-instrument tips disposed in engagement with and flush against the distal end faces 334 and 336 of respective endoscope insertion members 338 and 340. Thus, rigid distal portions of endocopic instrument assemblies deployable as discussed herein may have different shapes or configurations.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An endoscopic instrument assembly, comprising an endoscope, and a flexible medical instrument to be used in conjunction with said endoscope, wherein;

said endoscope includes a working channel having an internal diameter, and a distal end surface disposed perpendicular to an axis of said endoscope, said distal end surface having an outer perimeter, and one or more operative features of said endoscope, said operative features being positioned upon said distal end surface; and said flexible medical instrument includes a shaft sized to be passably insertable into said working channel of said endoscope, and an end effector removably attachable to a distal end of said shaft, said end effector being larger than said internal diameter of said working channel of said endoscope;

said end effector being shiftable in a distal direction, and being adapted to be disposed entirely within said perimeter of, and flush against said distal end surface of said endoscope during delivery of said flexible medical instrument, so that said end effector does not extend beyond said perimeter, and does not obstruct said operative features when said flexible medical instrument is in a delivery configuration, and wherein said end effector is shifted distal to, and apart from said distal end surface of said endoscope when in an operating configuration.

2. The flexible medical instrument defined in claim 1, wherein said end effector includes a suturing needle and wherein said suturing needle end effector includes a holder member for said suturing needle.

3. The flexible medical instrument defined in claim 2 wherein said needle is fixedly attached to said holder member.

4. The flexible medical instrument defined in claim 1, wherein said instrument shaft includes a spring biased pivotable stem section, said end effector being rigidly connected to said stem section.

5. An endoscopic instrument assembly, comprising an endoscope, and a flexible cutting instrument to be used in conjunction with said endoscope, wherein;

said endoscope includes a working channel having an internal diameter, and a distal end surface disposed perpendicular to an axis of said endoscope, said distal end surface having an outer perimeter, and one or more operative features of said endoscope positioned upon said distal end surface; and said flexible cutting instrument includes a flexible shaft insertable through said working channel of said endoscope, and a cutting end effector being shiftable in a distal direction, said cutting end effector being removably attachable to a distal end of said shaft, said end effector being larger than said internal diameter of said working channel of said endoscope; wherein said cutting end effector being adapted to be disposed entirely within said perimeter of, and flush against said distal end surface of said endoscope during delivery of said flexible cutting instrument, so that said end effector does not extend beyond said perimeter, and does not obstruct said operative features when said flexible cutting instrument is in a delivery configuration, and wherein said end effector is shifted distal to, and apart from said distal end surface of said endoscope when in an operating configuration.

6. The flexible cutting instrument defined in claim 5, wherein said end effector includes one or more rigid arms and a wire element extending therefrom.

7. An endoscopic instrument assembly, comprising an endoscope, and a flexible cutting instrument to be used in conjunction with said endoscope, wherein;

said endoscope includes a working channel having an internal diameter and a distal end surface disposed perpendicular to an axis of said endoscope, said distal end surface having an outer perimeter, and one or more operative features of said endoscope positioned upon said distal end surface; and said flexible cutting instrument includes a flexible shaft insertable through said working channel of said endoscope, and a cutting end effector being shiftable in a distal direction, said cutting end effector being removably attachable to a distal end of said shaft, said end effector being larger than said internal diameter of said working channel of said endoscope; wherein said cutting end effector being adapted to be disposed entirely within said perimeter of, and flush against said distal end surface of said endoscope during delivery of said flexible cutting instrument, so that said end effector does not extend beyond said perimeter, and does not obstruct said operative features when said flexible cutting instrument is in a delivery configuration, and wherein said end effector is shifted distal to, and apart from said distal end surface of said endoscope when in an operating configuration; and said instrument shaft includes a pivotable stem section that said end effector is rigidly connected thereto.

8. An endoscopic instrument assembly, comprising an endoscope, and a flexible suturing instrument to be used in conjunction with said endoscope, wherein;

said endoscope includes a working channel having an internal diameter, and a distal end surface disposed perpendicular to an axis of said endoscope, said distal end surface having an outer perimeter, and one or more operative features of said endoscope positioned upon said distal end surface ; and said flexible suturing instrument includes a flexible shaft insertable through said working channel of said endoscope, and a suturing needle end effector being shiftable in a distal direction, said suturing needle end effector being removably attachable to a distal end of said shaft, and said end effector being larger than said internal diameter of said working channel of said endoscope; wherein said suturing needle end effector being adapted to be disposed entirely within said perimeter of, and flush against said distal end surface of said endoscope during delivery of said flexible suturing instrument, so that said suturing needle end effector does not extend beyond said perimeter, and does not obstruct said operative features when said flexible suturing instrument is in a delivery configuration, and wherein said suturing needle end effector is shifted distal to, and apart from said distal end surface of said endoscope when in an operating configuration.

* * * * *